United States Patent
Keller et al.

(10) Patent No.: US 9,695,467 B2
(45) Date of Patent: Jul. 4, 2017

(54) METHOD FOR PROCESSING NUCLEIC ACIDS-CONTAINING FLUIDS

(71) Applicant: Roche Molecular Systems, Inc., Pleasanton, CA (US)

(72) Inventors: Reto Keller, Einsiedeln (CH); Thomas Meyer, Cham (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 52 days.

(21) Appl. No.: 14/553,151

(22) Filed: Nov. 25, 2014

(65) Prior Publication Data

US 2015/0079586 A1   Mar. 19, 2015

Related U.S. Application Data

(62) Division of application No. 12/623,757, filed on Nov. 23, 2009, now Pat. No. 8,921,094.

(30) Foreign Application Priority Data

Nov. 28, 2008   (EP) ..................... 08170315

(51) Int. Cl.
  *C12Q 1/68*   (2006.01)
  *B01L 7/00*   (2006.01)
  (Continued)

(52) U.S. Cl.
  CPC .............. *C12Q 1/6806* (2013.01); *B01L 7/52* (2013.01); *B03C 1/288* (2013.01); *B01L 9/523* (2013.01);
  (Continued)

(58) Field of Classification Search
  CPC ...... B01L 2300/0829; B01L 2300/1805; B01L 2300/1822; B01L 2300/1844; B01L 7/52;
  (Continued)

(56) References Cited

U.S. PATENT DOCUMENTS

| | | | |
|---|---|---|---|
| 4,447,395 A | 5/1984 | Englar et al. | |
| 5,102,623 A | 4/1992 | Yamamoto et al. | |

(Continued)

FOREIGN PATENT DOCUMENTS

| | | |
|---|---|---|
| DE | 19834584 | 2/2000 |
| EP | 1081234 | 3/2001 |

(Continued)

OTHER PUBLICATIONS

Tack and Reznik, Walk-Away Magnetic Bead-Based DNA Purification Using the JANUS Automated Workstation:; Application Note, PerkinElmer, May 2008.

(Continued)

*Primary Examiner* — Gautam Prakash
(74) *Attorney, Agent, or Firm* — Dinsmore & Shohl LLP

(57) ABSTRACT

A system and method for the processing of nucleic acids containing fluids involving manipulation of magnetically responsive particles contained therein are disclosed. In the system, a holder holds a plurality of containers containing the fluids, a heating device applies thermal energy to the fluids for incubation, and a separating device magnetically separates the particles. The heating and separating devices move into at least one operative position for processing the fluids and at least one inoperative position with respect to the containers, in which the containers are kept stationary at least during and in-between incubating the fluids and manipulating the magnetically responsive particles.

8 Claims, 6 Drawing Sheets

(51) Int. Cl.
*B01L 9/00* (2006.01)
*B03C 1/28* (2006.01)
*G01N 35/00* (2006.01)

(52) U.S. Cl.
CPC ............... *B01L 2200/0668* (2013.01); *B01L 2300/0829* (2013.01); *B01L 2300/1805* (2013.01); *B01L 2300/1822* (2013.01); *B01L 2300/1844* (2013.01); *G01N 35/0098* (2013.01); *G01N 2035/00574* (2013.01); *Y10T 436/113332* (2015.01); *Y10T 436/114165* (2015.01)

(58) Field of Classification Search
CPC .. B01L 9/523; B01L 2200/0668; B03C 1/288; G01N 35/0098; G01N 2035/00574
USPC ........ 422/63, 64, 67, 552; 435/287.1, 287.2, 435/287.3; 436/47, 48
See application file for complete search history.

(56) References Cited

U.S. PATENT DOCUMENTS

| | | | |
|---|---|---|---|
| 5,419,871 | A | 5/1995 | Muszak et al. |
| 5,459,073 | A | 10/1995 | Ryan |
| 5,603,160 | A | 2/1997 | Lessard et al. |
| 5,779,907 | A | 7/1998 | Yu |
| 5,906,796 | A | 5/1999 | Blevins et al. |
| 5,973,138 | A | 10/1999 | Collis |
| 6,368,561 | B1 | 4/2002 | Rutishauser et al. |
| 6,607,662 | B1 | 8/2003 | Ikeda et al. |
| 6,767,512 | B1 | 7/2004 | Lurz et al. |
| 7,033,543 | B1 | 4/2006 | Panzer et al. |
| 2002/0098117 | A1 | 7/2002 | Ammann et al. |
| 2003/0059823 | A1 | 3/2003 | Matsunaga et al. |
| 2007/0077648 | A1 | 4/2007 | Okamoto et al. |

FOREIGN PATENT DOCUMENTS

| | | |
|---|---|---|
| EP | 0977037 | 2/2002 |
| EP | 0977039 | 2/2002 |
| EP | 1260583 | 11/2002 |
| EP | 1278067 | 1/2003 |
| EP | 1615037 | 7/2004 |
| GB | 2300258 | 10/1996 |
| WO | 9820975 | 5/1998 |
| WO | 00 62933 | 4/2000 |
| WO | 0021668 | 4/2000 |
| WO | 0105510 | 1/2001 |
| WO | 0189705 | 11/2001 |

OTHER PUBLICATIONS

JANUS Automated Workstation; http://www.perkinelmer.de/CMSResources/Images/44-73222BRO_JANUS_overview.pdf, no date.
PerkinElmer Introduces JANUS Automated Workstation at Mip Tec 2005:; http://www.businesswire.com/news/home/20050511005688/en/PerkinElmer-Introduces-JANUS-Automated-Workstation-MipTec-2005, Basel, Switzerland, May 2005.
"Should I wash or reuse QUADRA pipette tips?"; Nov. 2006, TOMTEC, http://www.tomtec.com/pages/applications/;df/washreusetips.pdf.
KU HTS—Instrumentation "Liquid Handling Systems"; prior to Nov. 2008; http://www.hts.ku.edu/index.php?page=newfolder:instrumentation.
"JANUS Forensic Workstation for High Throughput DNA Sample Processing"; PerkinElmer, Inc. 2007, pp. 1-4.
"Apricot Designs." TPS-384 total Pipetting Solution TM, LVL Techologies, 2006, pp. 1-12.

METHOD FOR PROCESSING NUCLEIC ACIDS-CONTAINING FLUIDS

TECHNICAL FIELD

Embodiments of the present invention relate generally to nucleic acids containing fluid processing and more particularly to a system and method for the automated processing of nucleic acids containing fluids involving manipulation of magnetically responsive particles contained therein.

BACKGROUND

Nucleic acids (DNA=deoxyribonucleic acid, RNA=ribonucleic acid) are frequently used as a starting material for various analyses and assays in medical and pharmaceutical research, clinical diagnosis and genetic fingerprinting which typically require high quantity nucleic acids input.

As a matter of routine, adequate quantities of nucleic acids may be readily obtained by means of in-vitro amplification techniques, e.g., based on the well-known polymerase chain reaction (PCR). Commonly, prior to amplification, extraction (purification) of nucleic acids is required which can be performed in a two-step process, with a first step of releasing the nucleic acids from their envelopes (e.g. cell membranes) and a second step of separating the released nucleic acids from the remainder.

While nucleic acids may be readily released by incubating the samples, separation of the released nucleic acids is somewhat more difficult. The nucleic acids, for instance, may be separated making use of the differing molecular weights of the various cell components in a centrifuge. Spinning down the cell components typically results in different density layers, so that the nucleic acids may be selectively removed by a pipette or any other suitable instrument. Another separation technique that has been in practical use since several years and, for instance, is described in U.S. Pat. No. 5,973,138, uses magnetically responsive particles, which can be made to bind reversibly to the nucleic acids. Applying a magnetic field causes the particle-bound nucleic acids to be drawn to and be held against the inner wall of the vessel containing the cell components, enabling the surrounding medium to be flushed away and replaced by another fluid to re-suspend the nucleic acids therein.

In consideration of the fact that there is an ongoing increase in genetic analyses and assays requiring amplified nucleic acids, a strong demand for the automated extraction of nucleic acids prior to their amplification is observed.

International patent application WO 00/45164 describes a robotic workstation for the automated extraction and amplification of nucleic acids. In such workstation, multi-well plates to be filled with the samples are arranged on a rotary deck that can be revolved around a central column. A tool mount block that may simultaneously be provided with several tools can be moved vertically along the central column, so that alignment of the multi-well plates with each of the tools can be achieved revolving the rotary deck around the central column. Hence, the multi-well plates must be horizontally transferred to reach alignment with the tools, which, however, causes an undesired risk of contamination and/or spilling of the fluids. In addition, fixation of the tools at the tool mount block and rotationally transferring the multi-well plates for their alignment with the tools requires much constructional space which undesirably enlarges the overall dimensions of the work station.

SUMMARY

It is against the above background that disclosed hereinafter are embodiments of the present invention that relate generally to nucleic acids containing fluid processing, and more particularly to a system and method for the automated processing of nucleic acids containing fluids involving manipulation of magnetically responsive particles contained therein. The system providing for the extraction of nucleic acids prior to their amplification has small dimensions relative to the prior art, is easy to manufacture and reliable in use and enables fast extraction of nucleic acids without enlarged risk of contamination and/or spilling of the fluids.

In one preferred embodiment, a system for the processing of nucleic acids containing fluids, involving manipulating magnetically responsive particles contained therein, is disclosed. The system comprises at least one rack to hold a plurality of containers containing the fluids; and at least two processing devices including a heating device to apply thermal energy to the fluids for incubation and a separating device to apply a magnetic field to separate magnetically said particles contained in said containers. The processing devices are fixed to at least one actuator, which moves each of the processing devices into at least one operative position and at least one inoperative position with respect to the containers, wherein the processing devices in the operative position process the fluids.

In another preferred embodiment, a method for the processing of nucleic acids containing fluids contained in a plurality of containers is disclosed. The method comprises applying thermal energy to said fluids by means of a heating device; and magnetically separating magnetically responsive particles contained in said containers by means of a separating device. The containers are kept stationary at least during and in-between said applying thermal energy and magnetically separating said particles.

Other and further embodiments, features, and advantages of the invention will appear more fully from the accompanying drawings, the following detailed description, and the appended claims.

BRIEF DESCRIPTION OF THE DRAWINGS

In the drawings like designations denote like or similar elements, and in which.

REFERENCE LIST

Figure 1:
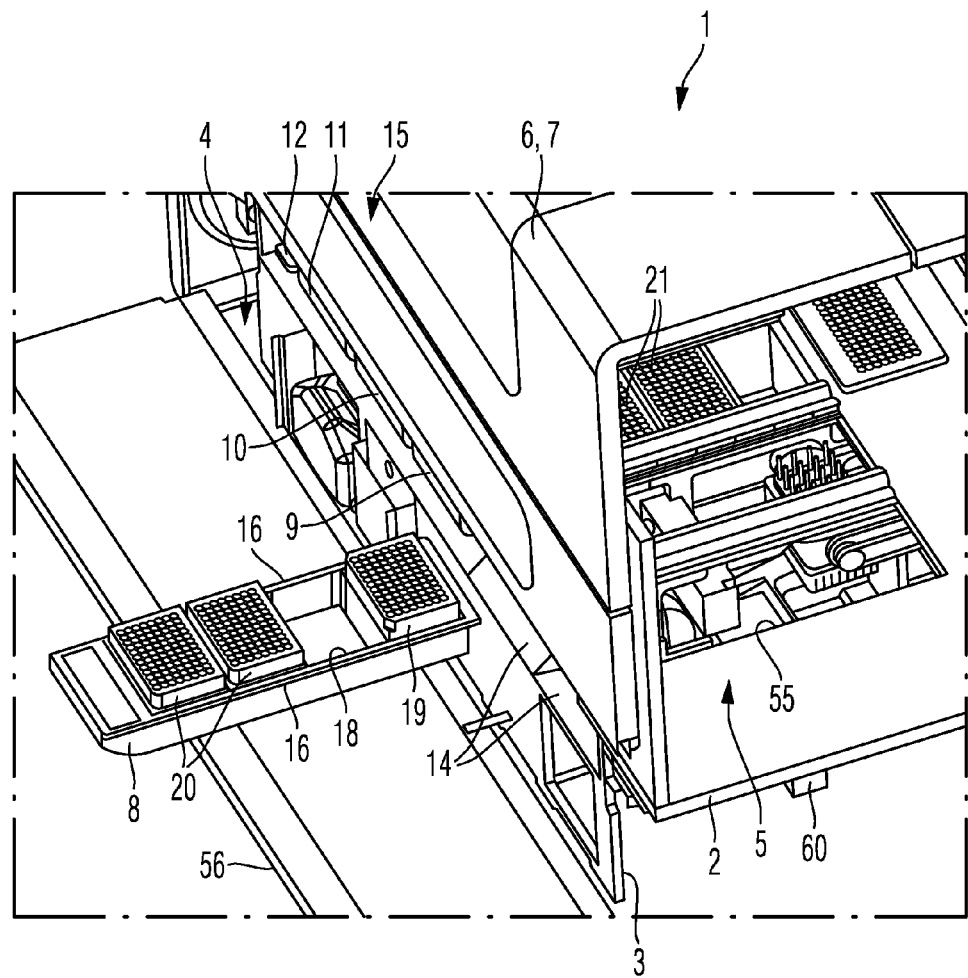
FIG. 1 is a schematic fragmentary perspective view of an exemplary embodiment of the system of the invention.

1 System
2 Work-plate

3 Substructure
4 Base plate
5 Cavity
6 Cover
7 System housing
8 Processing rack
9 Tip rack
10 First reagent rack
11 Second reagent rack
12 Bottle rack
13 Waste rack
14 Rack aperture
15 Front side
16 Rib
17 Groove
18 Retaining section
19 Processing plate
20 Output plate
21 Tip cartridge
22 Tip cartridge
23 Waste plate
24 Heating device
26 Heating pin
27 Magnetic pin
28 Carrier
29 First surface
30 Second surface
31 Supporting frame
32 First gearwheel
33 First electric motor
34 First gear belt
35 Vertical supporting plate
36 Vertical guiding rail
37 Spindle
38 Spindle nut
39 Second electric motor
41 Horizontal guiding rail
42 Third gearwheel
43 Third electric motor
44 Second gear-belt
45 Metallic plate
46 Cooling air channel
47 Outlet port
48 Air-guiding face
49 Inlet port
50 Rotational axle
51 Second gearwheel
52 Fourth gearwheel
53 Supporting rail
54 Cooling air conduit
55 Rack opening
56 Frontal lid
57 Well
58 Inner wall
59 Outer wall
60 Controller

DETAILED DESCRIPTION

According to one embodiment of the invention, a system for the automated processing of nucleic acids containing fluids (e.g. nucleic acids containing cell solutions) involving the steps of incubating the fluids to cause release (e.g. by cell lysis) of the nucleic acids into the surrounding medium and of manipulating magnetically responsive (i.e. magnetically attractable or magnetically repellable) particles contained in the fluids which can be made to reversibly bind to the released nucleic acids is disclosed.

The system for the processing of nucleic acids containing fluids comprises at least one holder, adapted to hold a plurality of containers for receiving nucleic acids containing fluids. In that, the holder may hold, e.g., at least one multi-well plate provided with a planar array of wells (containers).

The system further comprises at least two processing devices for the processing of the nucleic acids containing fluids which for extracting the nucleic acids include a heating device, adapted to apply thermal energy to the fluids contained in the containers for releasing the nucleic acids into the surrounding medium, and a separating device (i.e. magnetic field generation device), adapted to magnetically separate the magnetically responsive particles contained in said containers. In that, the separating device is adapted to apply at least one magnetic field to the nucleic acids containing fluids in order to magnetically interact with the magnetically responsive particles to, for instance, draw to, and hold the molecule-bound particles on the inner walls of the containers. Separating devices as such are well-known to those of skill in the art and, for instance, are described in German published patent application DE 19834584 A1 and British published patent application GB 2300258 A. For use with multi-well plates, the separating device includes a base plate provided with a plurality of magnetic pins with the magnetic pins being symmetrically arrayed such that each magnetic pin is surrounded by four wells of the multi-well plate. Applying axially oriented magnet fields (which are oriented orthogonal to the base plate) and/or diametrically oriented magnet fields (which are oriented in parallel alignment to the base plate) causes the particles to precipitate along the inner walls of the vessels facing a magnetic pin.

The system further comprises at least one actuator which the processing devices are fixed to, adapted to move each of the processing devices into at least one operative position and at least one inoperative position with respect to the containers, which preferably are kept stationary by the at least one holder during and in-between processing the fluids, wherein a processing device, when positioned in operative position, is operable to process the fluids, i.e. may be operated to interact with the fluids to achieve extraction of the nucleic acids, and, when positioned in inoperative position, is inoperable to process the fluids, i.e. cannot be operated to interact with the fluids to achieve extraction of the nucleic acids.

The system may further comprise at least one controller to control the system components which require control including the processing devices and the at least one actuator to move each of the processing devices into their operative and inoperative positions. The controller may be, for instance, embodied as programmable logic controller running a machine-readable program provided with instructions to perform operations in accordance with a predetermined process operation plan for the automated processing of the nucleic acids containing fluids.

The system may further comprise at least one pipettor (multi-pipetting device) which preferably is provided with a plurality of pipettes, adapted to transfer fluids to or from the containers.

The system may yet further comprise a nucleic acids amplification device, adapted for amplification of the extracted nucleic acids in order to establish an automated integrated nucleic acids extraction and amplification system.

The system, as described above, may be accommodated in a system housing for shielding the system from environmental (external) influences.

According to a preferred embodiment of the invention, the heating device, when in operative position, is in a position to contact the containers to enable heat transfer between the heating device and the fluids. Otherwise, when in inoperative position, the heating device is removed from the containers (i.e. assuming a position without having direct contact to the containers). Thus, enabling or disabling thermal conductance between the heating device and the containers in operative and inoperative positions, respectively, the nucleic acids containing fluids may quickly be heated for incubation and can otherwise rapidly cool-off which advantageously allows for a fast extraction of the nucleic acids and results in comparably short nucleic acids extraction periods.

According to another preferred embodiment of the invention, which advantageously may be combined with the above-described embodiment, the system comprises a cooling mechanism, adapted to actively cool the heating device when positioned in inoperative position. Providing for a cooling mechanism to actively cool the heating device strongly expedites cooling-off of the heating device following incubation and thus advantageously allows for a further reduction of the period required to extract the nucleic acids.

The cooling mechanism may use, for instance, streaming cooling air made to circulate around the heating device. In that, the cooling mechanism may be connected to an output of a cooling air generation device, which can be operated to generate streaming cooling air or may include at least one fan for generating streaming cooling air.

Alternatively, the cooling mechanism may include at least one thermoelectric cooling device, adapted for thermoelectrically cooling the heating device, such as a Peltier device utilizing the Peltier effect, which, e.g., contacts the heating device when in inoperative position. Stated more particularly, when passing an electric current through the Peltier device, it functions as heat pump, which can adsorb heat to thereby cool the heating device depending on the direction of current applied.

When actively cooling the heating device, it may be highly advantageous to further provide for a heat sink such as a metallic plate, adapted to contact the heating device when in inoperative position to conductively transfer heat from the heating device to the heat sink and to increase the surface that can be effectively used for actively cooling the heating device. Such heat sink may advantageously be used in combination with a thermoelectric cooling device thermally coupled to the heat sink.

According to yet another preferred embodiment of the invention, the processing devices for processing of the fluids are fixed to a common (single) carrier for moving into their operative and inoperative positions, respectively, which advantageously saves space to reduce the overall dimensions of the system. Moving each of the processing devices into operative and inoperative positions, respectively, preferably involves mutually revolving the processing devices around a common rotational axis which enables a highly compact construction of the system in which a processing device may either face the containers or can be turned away therefrom, so that a processing device can be easily moved into operative and inoperative positions. It may be preferable to arrange the heating and separating devices in opposite relationship with respect to each other which simplifies construction and allows the heating device to be easily (e.g. actively) cooled while the separation device is in operative position to be operated for separating the magnetically responsive particles.

In another embodiment, the system may enable the processing devices to access the containers from their bottom sides for processing of the fluids contained therein. This, for instance, may be achieved embodying the holder as a dedicated supporting member, typically a "rack", provided with at least one bottomless supporting portion (thus having an opening or through hole) for accommodating the plurality of containers. The rack may hold, for instance, at least one multi-well plate in the bottomless supporting portion.

In that case, it may be preferable to movably (e.g. slidably) support the rack by means of a structural member such as a work-plate to enable the rack to be moved between at least one loading/unloading position, adapted for loading/unloading a plurality of containers (e.g. at least one micro-well plate), and at least one processing position, adapted for processing the nucleic acids containing fluids contained in the containers. More specifically, when in loading/unloading position, the rack may reside inside, partly inside or outside a system housing, and, when in processing position, resides inside the system housing for processing of the fluids contained.

It may also be preferable to move a processing device from the bottom-side of the containers in operative position, which allows for a particularly small and compact system for processing of the nucleic acids containing fluids. In order to prevent the containers from being lifted upwardly when a processing device is moved into operative position, the rack or any other structural member of the system preferably is provided with at least one down-keeping member counteracting against upwardly (vertically) directed forces arising when moving the processing device into operative position to keep them in their regular position(s) as defined by the rack.

According to another embodiment of the invention, a method for the automated processing of nucleic acids containing fluids (e.g., nucleic acids containing cell solutions) that allows fast and reliable extraction of nucleic acids is disclosed. For extracting the nucleic acids, the method involves the steps of thermally incubating the fluids for releasing the nucleic acids and of manipulating magnetically responsive particles contained therein which can be made to reversibly bind to the released nucleic acids.

Accordingly, the method for the processing of nucleic acids containing fluids involves the use of magnetically responsive particles which, after providing a plurality of nucleic acids containing fluids, comprises performance of at least two processing steps for processing of the fluids by means of at least two processing devices, which are respectively moveable between at least one operative position and at least one inoperative position with respect to the containers.

The method includes a step of applying thermal energy to the nucleic acids containing fluids by means of a heating device, and a step of magnetically separating magnetically responsive particles contained in the containers by means of a separating device (i.e. a magnetic field generation device which can apply one or more magnetic fields to the fluids for magnetically manipulating the magnetically responsive particles contained therein), wherein the containers are kept stationary at least during and in-between said steps of applying of thermal energy and magnetically separating the particles.

According to a preferred embodiment of the invention, the heating device is actively cooled by means of a cooling mechanism when in inoperative position which advantageously enables small nucleic acids extraction periods.

According to yet another preferred embodiment of the invention, a processing device is forwarded from the bottom-sides of the containers into operative position, which advantageously allows for particularly easy processing of the nucleic acids containing fluids.

According to yet another preferred embodiment of the invention, moving of a processing device into operative and inoperative positions, respectively, involves mutually revolving the processing devices around a common rotational axis, which advantageously enables the processing devices to be readily used.

Now referring to FIGS. 1 to 6, exemplary embodiments of the system and method according to the invention are explained in greater details.

Accordingly, a system 1 for the processing of nucleic acids containing fluids (e.g., nucleic acids containing cell solutions) is described which permits extraction of the nucleic acids prior to amplification.

The system 1 includes a horizontal work-plate 2, which is supported by a substructure 3 and covered by a cavity 5 forming cover 6. The substructure 3, which is not further detailed herein, is supported by a horizontal base plate 4 upon which the system 1 may be placed on a laboratory bench or any other suitable surface. The cover 6, a base plate 4 and a hinged frontal lid 56, together with side and back plates (not shown in the figures), mutually compose a system housing 7 for accommodating the system 1 and shielding the system 1 from external influences.

Figure 2:
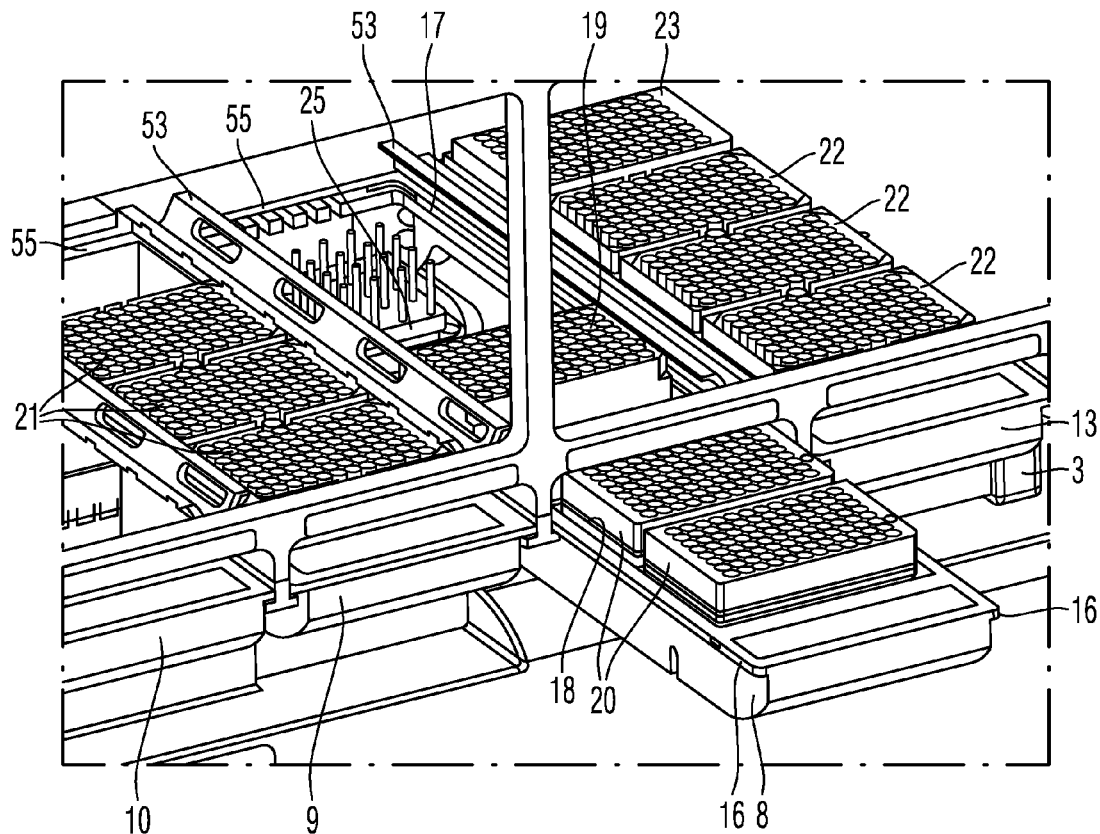
FIG. 2 is an enlarged fragmentary perspective view of the system of FIG. 1.
Figure 3:
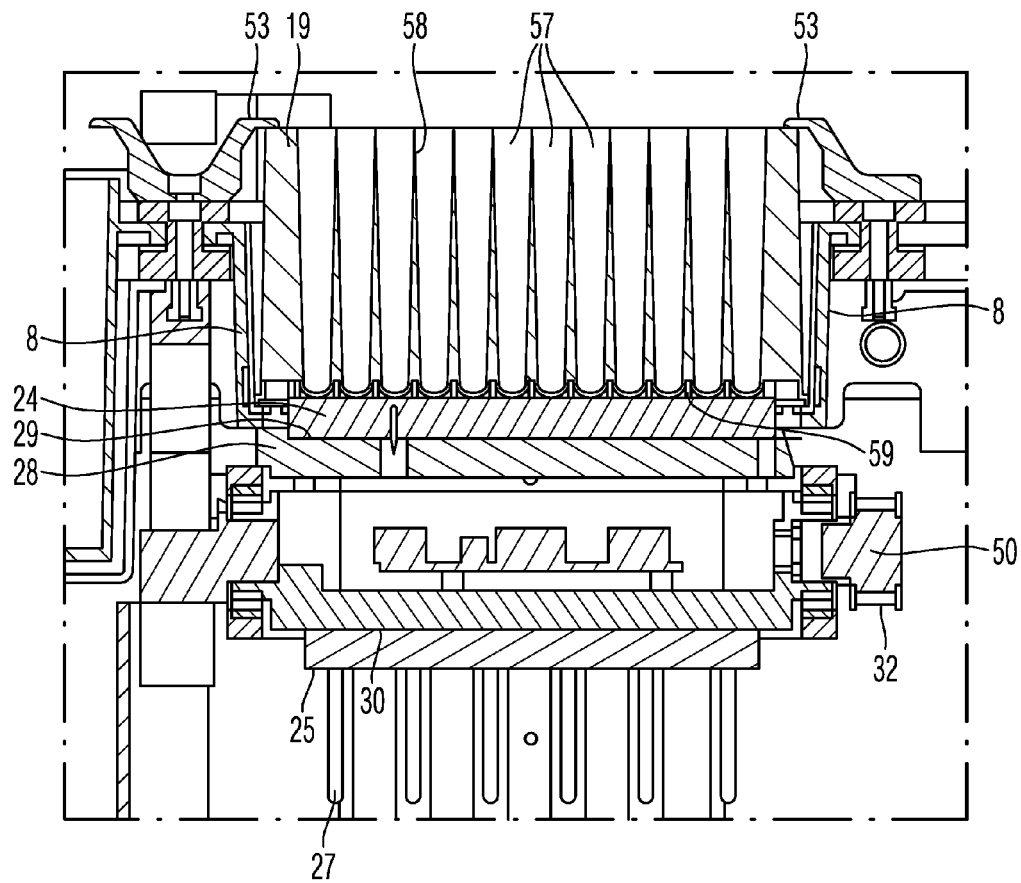
FIG. 3 is a fragmentary sectional view of the system of FIG. 1.
Figure 4:
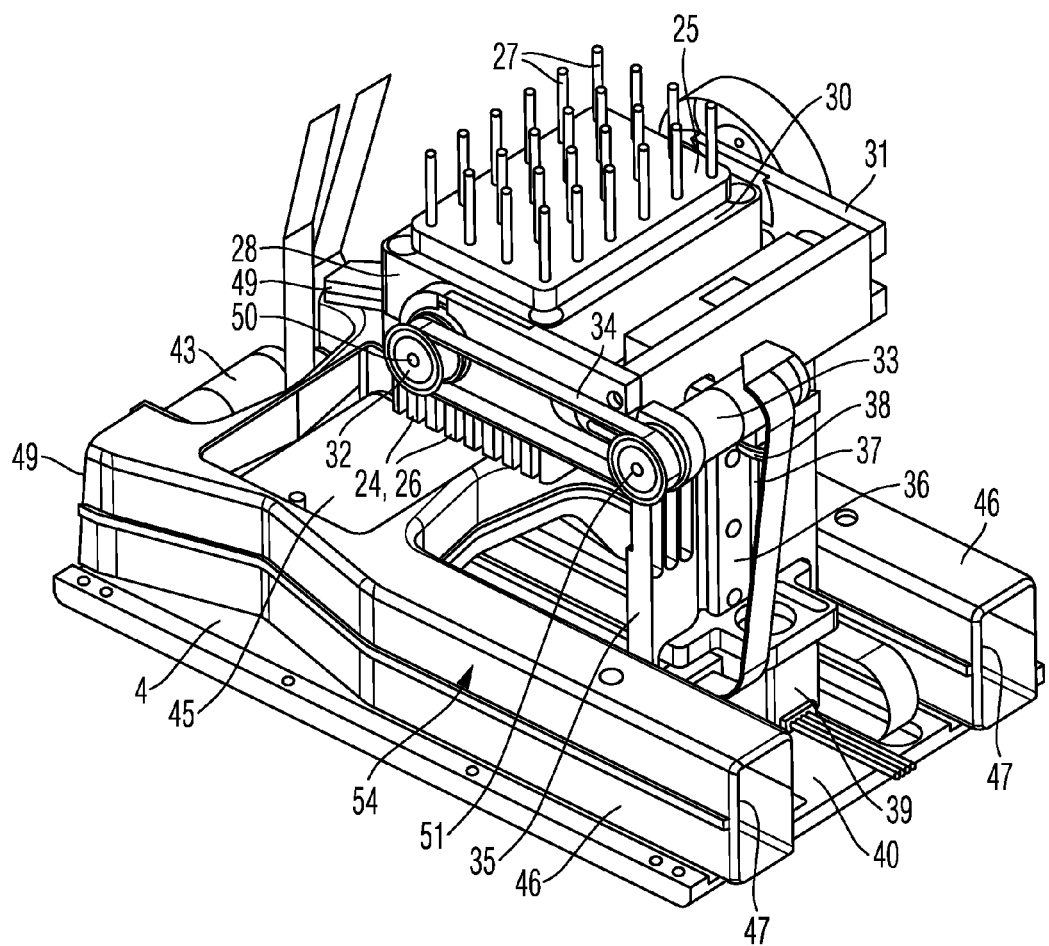
FIG. 4 is another enlarged fragmentary perspective view of the system of FIG. 1 illustrating the processing devices.
Figure 5:
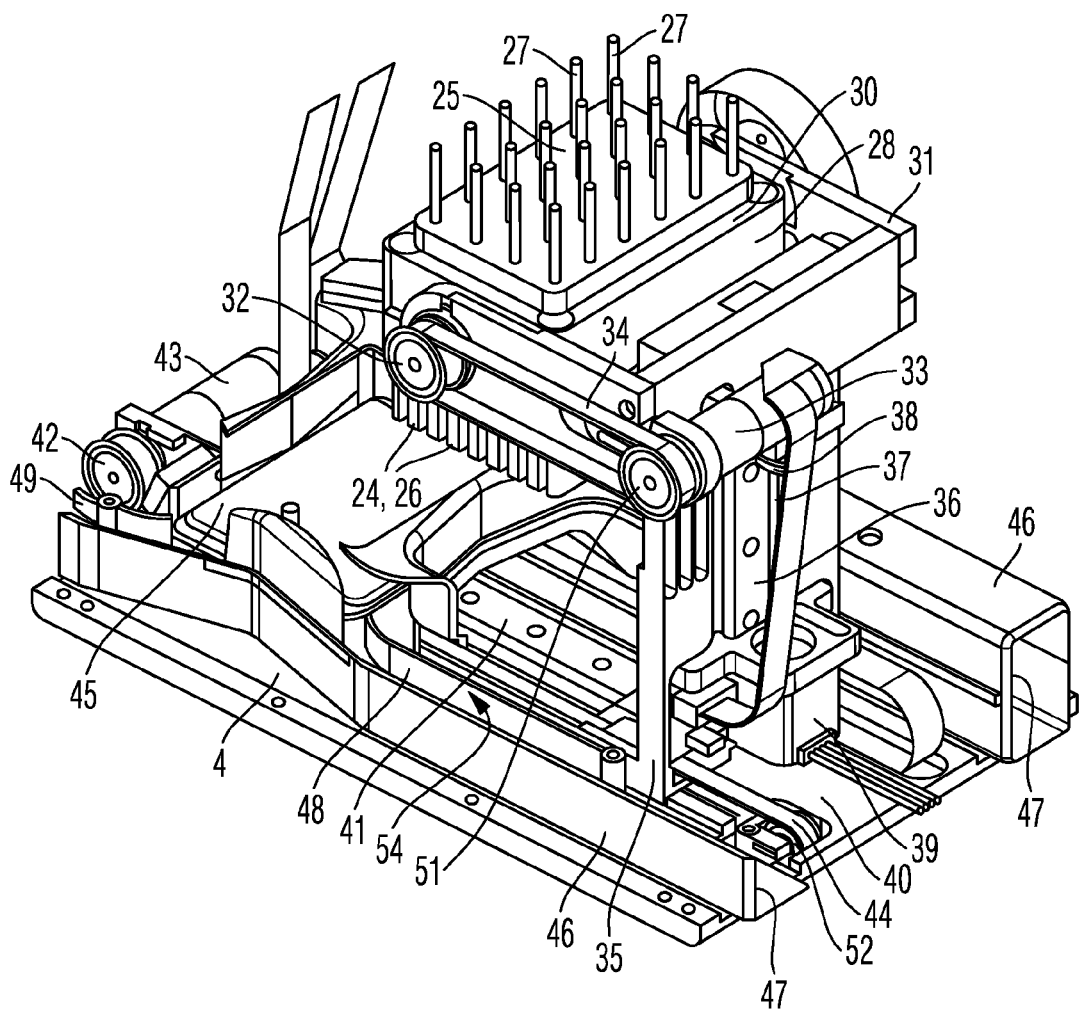
FIG. 5 is another enlarged fragmentary perspective view of the system of FIG. 1 illustrating the processing devices.

As depicted in FIGS. 1 and 2, the work-plate 2 is provided with a plurality of rack openings 55 arranged side by side with respect to each other, each of which being adapted for accommodating elongated racks 8-13. Each rack opening 55 may be accessed by a slot-like rack aperture 14 at a front side 15 of the system 1 allowing the racks 8-13 to be inserted into the rack openings 55 and removed therefrom, respectively. Each rack 8-13 is provided with two lateral ribs 16 linearly extending in parallel relationship with each other which, when inserting the racks 8-13 into the rack openings 55, get into fitting engagement with grooves 17 formed by the work-plate 2 to slidably support the racks 8-13.

More specifically, the system 1 comprises six racks 8-13 including a processing rack 8, a tip rack 9, a first reagent rack 10, a second reagent rack 11, a bottle rack 12, and a waste rack 13. Each rack has a number of retaining sections 18 for accommodating and holding various objects such as multi-well plates, tip cartridges, and bottle cartridges. In FIGS. 1 and 2, the processing rack 8 is shown to be loaded with three multi-well plates, which is a processing plate 19 to be filled with nucleic acids containing fluids used as starting materials for the extraction of nucleic acids and two output plates 20 to be filled with solutions containing the extracted (purified) nucleic acids. The processing plate 19 and the output plates 20 are micro-well plates in one embodiment, which are also known as microtiter plates, and in another embodiment may be generally a plurality of containers. The tip rack 9 is loaded with three tip cartridges 21 that may be filled with tips, the first and second reagent racks 10, 11 may be loaded with various processing solutions such as buffer and wash solutions which is not further detailed in the figures, the bottle rack 12 may be loaded with plural bottle cartridges to be filled with bottles containing various liquids such as suspensions of magnetically responsive particles which is also not further detailed in the figures, and the waste rack 13 is loaded with three empty tip cartridges 22 to receive waste tips and a waste plate 23 to receive waste liquids arising in processing the nucleic acids containing fluids.

While FIGS. 1 and 2 depict specific numbers of trays, retaining sections, plates and cartridges, it is to be understood that their numbers may vary in accordance with specific needs for the extraction of nucleic acids.

As illustrated, the processing rack 8 holds the processing plate 19 to be filled with the nucleic acids containing fluids used as starting materials for the nucleic acids extraction. For that purpose, the processing rack 8 is provided with two bottomless retaining sections 18 for holding one or two processing plates 19, which may be accessed from their bottom-sides for processing of the nucleic acids containing fluids contained therein. While two bottomless retaining sections 18 and only one processing plate 19 are shown in FIGS. 1 and 2, it is to be understood that the numbers of bottomless retaining sections 18 as well as processing plates 19 accommodated therein may vary in accordance with specific needs for the extraction of nucleic acids.

As exemplified in the present embodiment, the processing plate 19 includes a planar array of 96 deep wells that may be filled with the nucleic acids containing fluids used as starting materials for the nucleic acids extraction. Consistently therewith, 96-tip cartridges and 96-well plates are loaded onto the racks to be used in processing the nucleic acids containing fluids. It, however, is to be understood that differently sized arrays may alternatively be used in accordance with specific needs for the extraction of nucleic acids.

The racks 8-13 may be (e.g. completely) put out of the system housing 7 for loading and/or unloading with objects as above-detailed. Specifically, the processing rack 8 can be put out of the system housing 7 to, for instance, be loaded with the processing plate 19 that may be pre-filled with the nucleic acids containing fluids in a loading/unloading position to then be replaced in processing position for processing of the nucleic acids containing fluids contained therein. More specifically, in processing position, the nucleic acids containing fluids contained in the processing plate 19 may be processed for the extraction of nucleic acids by means of processing devices which include a heating device 24 adapted to generate Ohmic heat and a magnetic fields generation or magnetic device 25 both of which are arranged underneath the processing rack 8.

Stated more particularly, the heating device 24 is provided with a planar array of projecting heating pins 26 arranged in accord with voids formed in-between the wells 57 of the processing plate 19 so that the heating pins 26 can dip into the voids when the heating device 24 is moved towards the processing plate 19. Applying an electric current to the heating device 24 causes the heating pins 26 to generate Ohmic heat to apply thermal energy to the nucleic acid containing fluids contained in the wells 57 of the processing plate 19.

Analogously, the magnetic device 25 is provided with a planar array of projecting magnetic pins 27 arranged in accord with the voids in-between the wells 57 of the processing plate 19, so that the magnetic pins 27 can dip into the voids when the magnetic device 25 is moved towards the processing plate 19. The magnetic pins 27 are made of magnetically hard (permanently magnetized) material, which, when dipping into the voids in-between the wells 57, causes the molecule-bound magnetically responsive (attractable) particles contained in the fluids to be drawn to and hold on the inner walls 58 of the wells 57 which are filled with the nucleic acids containing fluids. It is to be understood, that the magnetic pins 27 might alternatively be embodied as electromagnets, which can be selectively magnetized when applying an electric current.

Both the heating and magnetic devices 24, 25 are fixed to a carrier 28, with the heating device 24 being fixed to a first surface 29 of the carrier 28 and the magnetic field generation device 25 being fixed to a second surface 30 of the carrier 28 which is in opposite relationship to the first surface 29. A supporting frame 31 surrounding the carrier 28 rotatably supports the carrier 28 to be rotated around a horizontally aligned rotational axis 50. The carrier 28 is rotatably driven by means of a first gear belt drive including an axis-centered first gearwheel 32 which is connected to the carrier 28 and rotates therewith and a first DC electric motor 33 that is fixedly attached to the supporting frame 31 and drives a second gearwheel 51 connected to the first gearwheel 32 by means of a first gear belt 34. Applying an electric current to the first DC electric motor 33 rotates the carrier 28 around rotational axis 50, so that the first and second surfaces 29, 30 of the carrier 28 may alternatively either face the processing plate 19 or turned away therefrom.

The supporting frame 31 is connected to a vertical supporting plate 35 which vertically slidably supports the supporting frame 31 to be movable along vertical guiding rail 36 fixed to the vertical supporting plate 35. The supporting frame 31 is slidably driven by means of a spindle drive including spindle 37 that is connected to the supporting frame 31 by means of spindle nut 38. The spindle 37 is rotatably driven by a second DC electric motor 39 such as a stepper motor, which is fixedly attached to the vertical supporting plate 35. Applying an electric current to the second DC electric motor 39 turns the spindle 37 to translationally move the supporting frame 31 in vertical direction to thereby increase or decrease a vertical distance between the carrier 28 and the processing rack 8.

The vertical supporting plate 35 is fixedly attached to a horizontal supporting plate 40 slidably supported by the base plate 4 to be horizontally moveable along horizontal guiding rail 41 that is fixed to the base plate 4. The horizontal supporting plate 40 is driven by means of a second gear belt drive which includes a third DC electric motor 43 fixed to the base plate 4 and driving a third gearwheel 42 connected to a fourth gearwheel 52 supported by the horizontal supporting plate 40 by means of a second gear belt 44. Applying an electric current to the third DC electric motor 43 causes the horizontal supporting plate 40 to be translationally moved along horizontal guiding rail 41, so that the carrier 28 can be horizontally aligned with each of the retaining sections 18 of the processing rack 8 and micro-well plates accommodated therein, respectively, such as processing plate 19.

Accordingly, rotationally and/or vertically and/or horizontally moving the carrier 28, the heating and magnetic field generation devices 24, 25 may be selectively moved between their operative and inoperative positions with respect to the processing plate 19. In operative position, the heating pins 26 dip into the voids of the wells 57 of the processing plate 19 to have direct contact with the outer walls 59 of the wells 57 to conductively transfer heat thereto. Analogously, in operative position, the magnetic pins 27 dip into the voids in-between the wells 57 of the processing plate 19 to apply plural magnetic fields to the nucleic acid containing fluids for the separation of molecule-bound magnetic particles contained therein. For example, starting with the heating device 24 being in operative position, the magnetic device 25 can be brought in operative position vertically lowering the carrier 28, turning it by 180°, and vertically lifting it towards the processing plate 19. Moving the magnetic field generation device 25 into operative position thus automatically transfers the heating device 24 into inoperative position, and vice versa. In order to avoid any vertical translational movement of the processing plate 19 when bringing the heating and magnetic field generation devices 24, 25 in operative position contacting the outer walls 59 of the wells 57, supporting rails 53 extending along the rack openings 55 are provided for keeping the processing plate 19 down in regular position.

A programmable logic controller 60 running a machine-readable program (computer-program) provided with instructions to perform operations in accord with a predetermined process operation plan for the automated extraction of nucleic acids processing of the nucleic acids containing fluids is electrically connected to the system components requiring control. The controller 60 receives information from these system components and generates and transmits corresponding control signals according to the process operation plan. It, in particular, controls movements of the carrier 28 and processing of the heating and magnetic field generation devices 24, 25.

Figure 6:
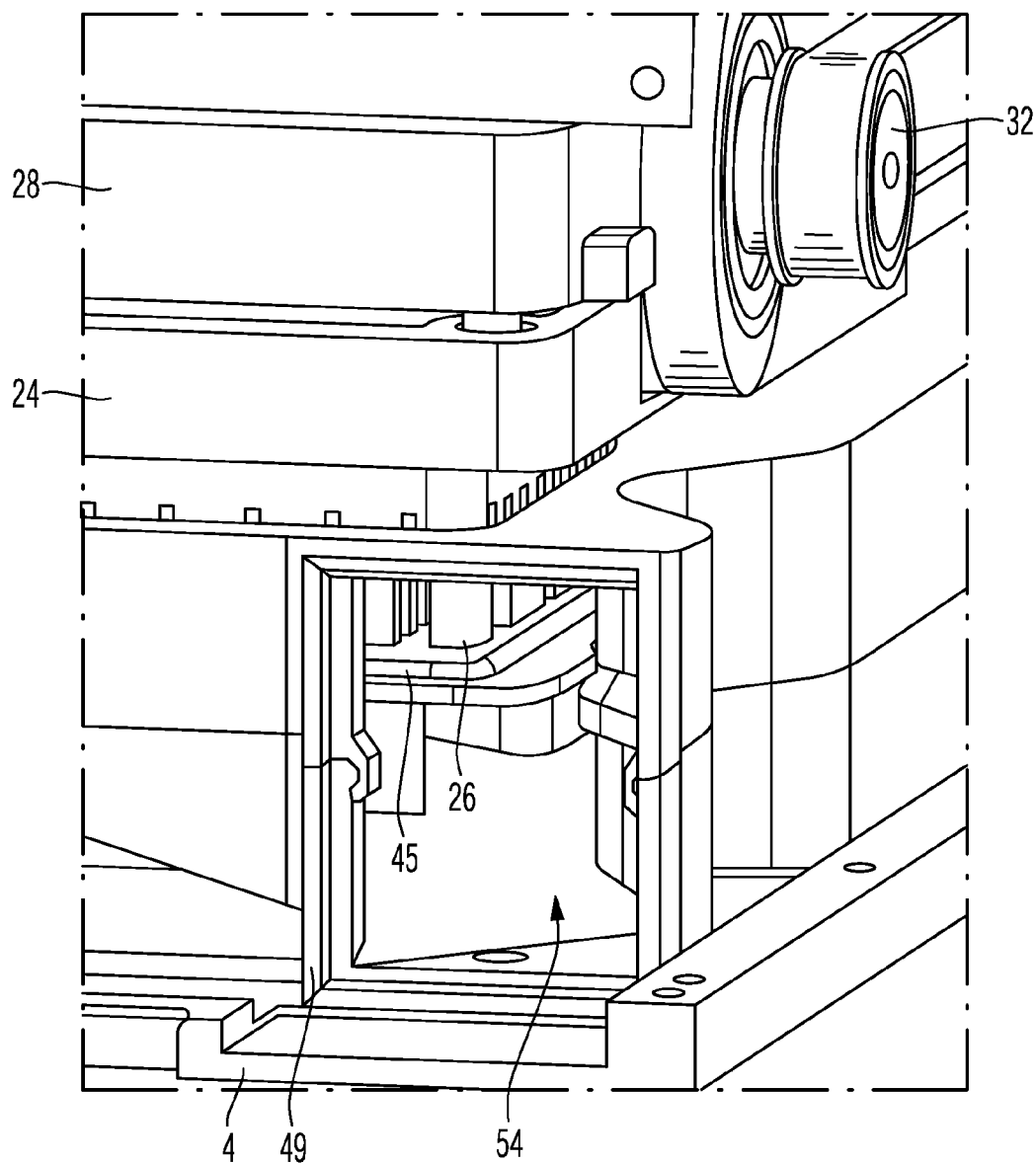
FIG. 6 is another enlarged fragmentary perspective view of the system of FIG. 1 illustrating the heating device contacting the metallic heat sink.

The system 1 further comprises a horizontally aligned metallic plate 45 for instance made of aluminum used as heat sink for the heating device 24 when in inoperative position. As illustrated in FIG. 6, the heating device 24 may be placed onto the metallic plate 45 to conductively transfer heat from the heating device 24 to the metallic plate 45 to accelerate cooling-off of the heating device 24.

The system 1 further comprises a cooling air conduit 54 accommodating the metallic plate 45 and enabling streaming cooling air to flow against both the upper and lower sides of the metallic plate 45. More specifically, a pair of cooling-air channels 46 that may be charged with cooling air at inlet ports 49 unifies upstream the metallic plate 45, particularly using air-guiding faces 48 to make the cooling air efficiently flow against the heat sink or metallic plate 45 and heating device 24 brought in contact therewith, and then again separate downstream the metallic plate 45 to discharge the cooling air at outlet ports 47. The metallic plate 45 and the heating device 24 placed on the metallic plate 45 can thus be actively cooled by means of cooling air. Upon doing so, since the heating device 24 is in direct contact with the heat sink or metallic plate 45, the surface, which can be effectively used for actively cooling the heating device, can be advantageously increased. The cooling air may be provided by a fan (not shown in the figures) or, alternatively, using exhaust air of another air-cooling system. Yet alternatively, a Peltier device can be used for actively cooling the metallic plate 45 and heating device 24, respectively.

While not shown in the figures, the system 1 further includes at least one pipettor (multi-pipetting device) that is provided with a plurality of pipettes (pipetting ducts) adapted to transfer fluids to or from the multi-well plates of the system 1.

While not shown in the figures, the system 1 may further include a nucleic acid amplification device adapted for amplification of the extracted nucleic acids in order to establish an automated integrated nucleic acid extraction and amplification system.

Now, an exemplary embodiment for the extraction of nucleic acids using the system 1 is explained. The process starts with providing a plurality of nucleic acids containing fluids (e.g. cell solutions) such as blood samples, which are directly pipetted into wells of the processing plate 19 to be used as starting materials for the nucleic acids extraction. The processing plate 19 may, for instance, be pre-filled with the cell samples and loaded onto the processing rack 8 when the processing rack 8 is positioned in loading/unloading position outside the system housing 7 to then be inserted into the rack opening 55. Alternatively, the processing plate 19 is already filled with the cells samples when the processing rack 8 is being placed in processing position for processing by means of the heating and magnetic field generation devices 24, 25.

The nucleic acids containing fluids contained in the processing plate 19 are mixed with various solutions such as lysis and binding buffers, which facilitate lysis of the cells. Afterwards, the heating device 24 is moved towards the processing plate 19 from the bottom-sides thereof, so that the heating pins 26 dip into the voids in-between the wells 57 of the processing plate 19 to directly contact the outer walls 59 of the wells 57. Upon applying electric current to the heating device 24, heat is conductively transferred to the samples to make the cells burst and release the nucleic acids into the surrounding medium. The processing plate 19 is kept stationary during incubation of the samples.

Before or after incubation, magnetically attractable particles are added to the samples, which are made to be bound to the released nucleic acid molecules. Subsequently, at least one magnetic separation step including manipulation of the molecule-bound particles is performed in which the magnetic field generation device 25 is moved towards the processing plate 19, so that the magnetic pins 27 can dip into the voids in-between the wells 57 of the processing plate 19 to thereby apply magnetic fields which cause the molecule-bound particles to be drawn to and hold on the inner walls 58 of the wells 57. When holding the molecule-bound particles on the inner walls 58 of the wells 57, supernatant fluids of the samples can be aspired and dispensed into the liquid waste plate 23 of the waste rack 13, followed by dispensing of wash buffer into the nucleic acids containing wells and removal of the magnetic pins 27 to re-suspend the molecule-bound particles in the wash buffer. Such magnetic separation step can be repeated several times. The processing plate 19 is kept stationary during and in-between incubation and magnetic separation steps.

Following incubation of the cells, the heating device 24 is placed onto the metallic plate 45 to transfer heat thereto and to actively cool the heating device 24 by streaming cooling air. More particularly, the heating device 24 may be placed on the metallic plate 45 in-between incubation and the magnetic separation steps and/or during the magnetic separation steps when the magnetic device 25 is inoperative and/or following the magnetic separation steps as appropriate.

Following removal of the magnetically attractable particles, the nucleic acids are re-suspended in elution buffer to obtain nucleic acids containing fluids to be used for nucleic acid amplification, which are transferred to one of the output plates 20 to be output for amplification.

In above method, various reagents and other fluids such as wash buffer and magnetically attractable particles used for the extraction of the nucleic acids are loaded onto the bottle rack 12 and onto the first and second reagent racks 10, 11 to be transferred to the processing plate 19 when appropriate. Magnetic glass particles which have a glass surface and a magnetic core may, for instance, be used for reversibly binding to the nucleic acids, which as is known to those of skill in the art can adsorb to nucleic acids in the presence of a chaotropic salt at a pH of more than 7. The nucleic acids may be eluted from the particles applying low-salt conditions and heat.

Hence, the system and method of the invention circumvent the problems of prior art nucleic acids extraction.

Keeping the processing plate 19 stationary (on its place) during and in-between incubation and magnetic separation steps advantageously reduces a risk of contamination and/or spilling of the samples when extraction of nucleic acids is performed. Otherwise, fixing the heating and magnetic field generation devices 24, 25 to a single carrier 28 for moving into operative and inoperative positions, respectively, advantageously allows for a small system size and fast performance of extraction steps. Providing for a metallic heat sink and active cooling by streaming cooling air advantageously reduces cooling-off of the heating device 24 when in inoperative position to thereby reduce nucleic acids extraction periods.

Accordingly, in one preferred embodiment, a system 1 for the processing of nucleic acids containing fluids, involving manipulating magnetically responsive particles contained therein, has been disclosed by the above discussion. The system 1 comprises at least one holder or rack 8 adapted to hold a plurality of containers 19 containing the fluids, and at least two processing devices including a heating device 24 adapted to apply thermal energy to the fluids and a separating device 25 adapted to separate magnetically the particles contained in the containers 19. The processing devices 24, 25 are fixed to at least one actuator 28-44, adapted to move each of the processing devices 24, 25 into at least one operative position and at least one inoperative position with respect to the containers 19, wherein a processing device 24, 25 in operative position is operable to process the fluids.

In another embodiment, the heating device 24 in operative position contacts the containers 19 and in inoperative position is removed from the containers 19.

In another embodiment, the system 1 further comprises a cooling mechanism 46-49, adapted to actively cool the heating device 24 in inoperative position.

In another embodiment, the system 1 further comprises a heat sink 45, adapted to contact the heating device 24 in inoperative position to conductively transfer heat from the heating device 24 to the heat sink 45.

In still another embodiment, the processing devices 24, 25 are fixed to a common carrier 28.

In another embodiment, the moving of the processing device 24, 25 into operative and inoperative positions, respectively, involves commonly revolving the processing devices around a single rotational axis.

In another embodiment, the holder or rack 8 is adapted to provide access to the containers 19 from their bottom sides.

In still another embodiment, the containers 19 are being hold by means of at least one rack 8 provided with at least one bottomless retaining section 18 for accommodating the containers 19.

In another embodiment, the rack 8 is movably supported by a work-plate 2, wherein the rack 8 is movable between at least a loading/unloading position, adapted for loading/unloading of containers 19, and at least a processing position, adapted for processing the fluids contained in the containers.

In another embodiment, the system 1 further comprises at least one pipettor provided with a plurality of pipettes, adapted to transfer fluids to or from the containers.

In still another embodiment, the system 1 further comprises at least one nucleic acids amplification device, adapted for amplifying nucleic acids.

In another preferred embodiment, a method for the processing of nucleic acids containing fluids contained in a plurality of containers 19 has been disclosed by the above discussion. The method comprises applying of thermal energy to the fluids by means of a heating device 24, and magnetically separating magnetically responsive particles contained in the containers 19 by means of a separating device. In the method, the containers 19 are kept stationary at least during and in-between the steps of applying thermal energy and magnetically separating the particles.

In another embodiment of the method, the heating device 24 is actively cooled by means of a cooling mechanism 46-49.

In still another embodiment of the method, a processing device 24, 25 is moved from the bottom-sides of the containers 19 in an operative position for processing the fluids.

In yet another embodiment of the method, moving of the processing devices 24, 25 into and in-between operative and inoperative positions involves commonly revolving the processing devices around a single rotational axis.

Obviously many modifications and variations of the present invention are possible in light of the above description. It is therefore to be understood, that within the scope of appended claims, the invention may be practiced otherwise than as specifically devised.

What is claimed is:

1. A method for the processing of nucleic acid-containing fluids contained in a plurality of containers, comprising:
   placing the plurality of containers comprising the nucleic acid-containing fluids in a holder,
   fixing the holder and nucleic acid-containing fluids into a stationary processing position;
   moving a heating device to an operative position beneath the containers and applying thermal energy to said fluids by means of the heating device;
   moving the heating device to an inoperative position while the holder and nucleic acid-containing fluids remain fixed in the stationary processing position;
   moving a separating device into an operative position; and
   magnetically separating magnetically responsive particles contained in said containers by means of the separating device in an operative position,
   wherein the containers comprising nucleic acid-containing fluids are kept stationary relative to the heating device and the separating device at least during and in-between said applying thermal energy and magnetically separating said particles.

2. The method as claimed in claim 1, further comprising actively cooling the heating device with a cooling mechanism in the inoperative position.

3. The method as claimed in claim 2, further comprising providing a heat sink to contact the heating device in the inoperative position to conductively transfer heat from the heating device to the heat sink.

4. The method as claimed in claim 1, further comprising moving the heating device and the separating device between operative and inoperative positions, wherein the heating device in operative position contacts the containers to apply the thermal energy and in the inoperative position is removed from the containers, and wherein the separating device in the operative position magnetically separates said particles and in the inoperative position is moved away from the containers.

5. The method as claimed in claim 4, wherein moving between the operative and the inoperative positions involves commonly revolving the heating device and the separating device around a single rotational axis.

6. The method as claimed in claim 1, further comprising accessing the containers from their bottom sides to apply the thermal energy and to magnetically separate the particles.

7. The method as claimed in claim 1, wherein the holder comprises a rack having at least one bottomless retaining section, and comprising accessing the containers from their bottom sides through the bottomless retaining section of the rack to apply the thermal energy and to magnetically separate the particles.

8. The method as claimed in claim 7, wherein accessing the containers from their bottom sides through the bottomless retaining section of the rack to apply the thermal energy and to magnetically separate the particles occurs in the processing position, and said method further comprises movably supporting the rack such that the rack is movable between at least a loading/unloading position for loading/unloading the containers, and the processing position.

* * * * *